US006468746B1

(12) United States Patent
Sieber et al.

(10) Patent No.: US 6,468,746 B1
(45) Date of Patent: Oct. 22, 2002

(54) METHOD FOR SELECTING STABILIZED PROTEINS

(75) Inventors: Volker Sieber, Dresden; Franz X. Schmid, Bayreuth, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/359,753

(22) Filed: Jul. 23, 1999

(51) Int. Cl.[7] .............................. C12Q 1/68; C12N 7/00; C12N 15/00; C12P 21/00; C07H 21/04

(52) U.S. Cl. ............................ 435/6; 435/5; 435/235.1; 435/320.1; 435/69.1; 435/69.7; 435/243; 536/23.4; 536/23.1

(58) Field of Search .............................. 435/5, 6, 320.1, 435/235.1, 69.1, 69.7, 91.4, 243; 536/23.1, 23.4

(56) References Cited

U.S. PATENT DOCUMENTS 5,514,548 A * 5/1996 Krebber et al. ................. 435/6

OTHER PUBLICATIONS

Sieber, et al. Nature Biotechnology 16: 955–960, Oct. 1998.*
Kristensen, et al. Folding & Design 3: 321–328, Jul. 9, 1998.*
Van Melderen, et al. Journal of Biological Chemistry (271) 44: 27730–27738, Nov. 1996.*
Brems et al., *Protein Eng.*, 5(6), 1992, 519–525.
Imoto, *CMLS*, 53, 1997, 215–223.
Shoichet etal., *Proc.Nat.Acad.Sci.*, 92(1), 1995, 452–6.
Pace et al., *FASEB Journal,* vol. 10, 1996, 75–83.
Fischer et al., *Protein Sci.,* 5, 1996, 947–955.
Bowie etal., *Curr.Opi.in Str.Biol.* 3(1), 1993, 437–44.
Smith, *Curr.Opi. in Biotech.,* 2, 1991, 668–673.
Georgiou et al., *Nature Biotech.,* 15, Jan. 1997, 29–34.
Mattheakis et al., *Meth. in Enzy.,* 267, 1996, 195–207.
Hanes et al., *Proc.Nat.Acad.Sci.,* 94(9), 1997, 4937–42.
Cull et al., *Proc.Nat.Acad.Sci.,* 89(5), 1991, 1865–69.
Krebber et al., *FEBS Letters,* 377(1), 1995, 227–231.
Parsell et al., *J. Biol. Chem.,* 264(13), 1989, 7590–95.
Krebber et al., *J. Mol. Biol.,* 268(3), 1997, 607–618.
Stemmer, *Nature,* vol. 370, Aug. 1994, 389–391.
Skinner et al., *Proc.Nat.Acad.Sci.,* 93(19), 1996, 10753–57.
Finkele et al., *Biochemistry,* 29, 1990, 8517–8521.

* cited by examiner

Primary Examiner—David Guzo
Assistant Examiner—Gerald G. Leffers, Jr.
(74) Attorney, Agent, or Firm—Keil & Weinkauf

(57) ABSTRACT

Proteins to be stabilized are incorporated between two domains of the gene III protein of a bacteriophage. A mixture of phages with a large repertoire of mutants of the protein to be stabilized in the gene III protein is treated with proteases. The phages which present the least stable variants of the protein lose their infectivity fastest, whereas those whose genes code for stabilized variants of the protein retain their infectivity longest. Infection of bacterial cells with the phages treated with proteases and multiplication thereof leads to enrichment of the phages which comprise genes of stabilized variants of the mutagenized protein. The sequences of the most stable variants of the protein are obtained in this way from the genomes of the phages remaining after several rounds of phage cultivation, proteolysis and reinfection.

18 Claims, 4 Drawing Sheets

METHOD FOR SELECTING STABILIZED PROTEINS

FIELD OF THE INVENTION

Figure 1A:
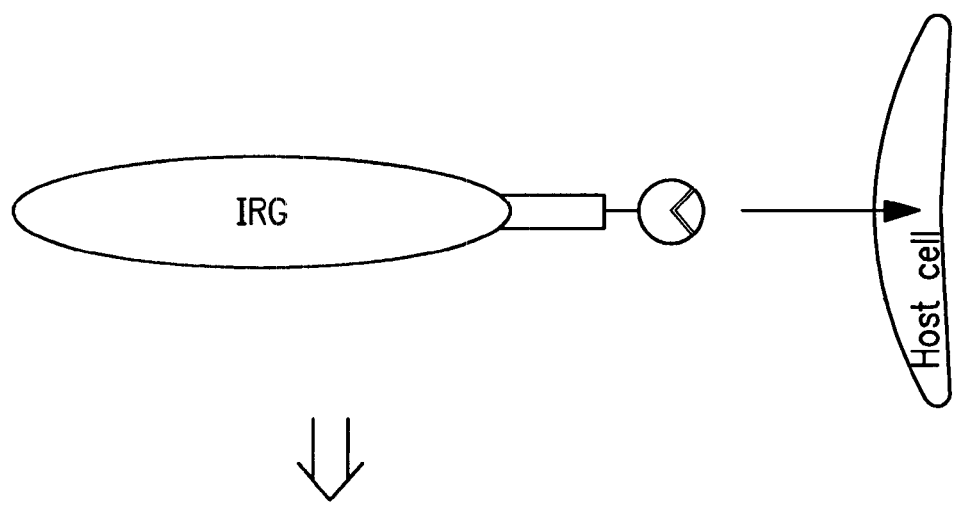

The invention described herein relates to a method for selecting proteins which have high stability. Specifically, it relates to a system with which it is possible to screen out and to isolate the most stable proteins from a large number of mutants thereof.

BACKGROUND OF THE INVENTION

Proteins are widely used as enzymes or biocatalysts in industrial biotechnological processes. As antibodies, receptors, vaccines or hormones, they have a great potential for use in medical diagnosis and therapy. Unfortunately, however, there are limitations on use both in industry and in medicine. These derive in particular from the stability of the proteins being too low (Martinek, K. and Mozhanev, V. V., 1993). Biotechnological processes often proceed under reaction conditions which are survived for only a short time by the enzymes employed. Organic solvents, extreme pH values or high temperatures, which are advantageous or even necessary for many reactions, may lead to rapid inactivation of the enzymes (Gupta, S. and Gupta, M. N., 1993). Increased stability proves to be advantageous in the preparation of proteins, too. Thus, in general, the yields and the purity of a prepared protein can be improved if it has increased stability. An increased stability also extends the shelf life of proteins and simplifies storage and transport (Brems, D. N. et al., 1992). It is therefore of great interest to increase the stability of proteins. In the first place, a distinction must be made between different types of stability. Thermal stability (toward denaturation and aggregation), conformational stability (toward organic solvents) and chemical stability (toward oxidation, modification of the side groups) are particularly important on use as biocatalysts. Resistance to proteases is important in the medical sector. The thermodynamic stability is a measure of the equilibrium between folded, native (active) protein and its unfolded, denatured (inactive) form. An increase in the thermodynamic stability thus means a shift in the equilibrium toward native protein. The various types of stability correlate reasonably well. This means that a protein thermodynamically stabilized in its conformation has generally also undergone a stabilization according to the other criteria. This derives from the fact that irreversible inactivation (e.g. aggregation, degradation) mostly originates from unfolded protein, or inactivating alterations (e.g. chemical modification) can be averted better (Imoto, T., 1997).

There are in principle two possibilities for increasing the stability of a protein. On the one hand, proteins can be stabilized by external factors (e.g. solvent, immobilization, chemical modification) (Gray, C. J., 1993, Tyagi, R. and Gupta, M. N., 1993, Cabral, J. M. S. and Kennedy, J. F., 1993). On the other hand, the intrinsic stability of a protein can be increased by altering its amino acid sequence by mutations. This latter method is also referred to as protein engineering. Whereas the first method, external stabilization, rapidly reaches its limits through the conditions of use of the protein, the advantage of protein engineering is that it is possible thereby to stabilize proteins for applications under various conditions. It should be noted in this connection that the optimization of proteins in their physiological environment is not for thermodynamic stabilization but for folding rate, flexibility and degradability in the cell also (Shoichet, B. K. et al., 1995). It must therefore be assumed that there is sufficient potential available for stabilization by mutations.

In protein engineering in turn there are two ways of proceeding. On the one hand, stabilizing mutations can be deliberately introduced and, on the other hand, the stabilizing mutations can be selected out of a large number of randomly generated ones. Targeted mutagenesis demands extensive knowledge about the stabilizing interactions in a protein in order to have some probability of success. It is true that the principal types of interactions are known (e.g. Pace, C. N. et al., 1996), and computer-assisted algorithms moreover sometimes come quite close to predicting protein structures from the amino acid sequence (Fischer, D. and Eisenberg, D., 1996, Bowie, J. U. and Eisenberg, D., 1993). However, results of predicting the effect of individual mutations remain unsatisfactory. Even if the spatial structure of the protein to be modified is known, it is scarcely possible to predict or calculate the effects of mutations on protein stability because, in the end, knowledge about the denatured state of the protein or alternative conformations is still lacking. However, it is possible to apply targeted mutagenesis if homologs of the protein used are already known from thermophilic organisms. It is then possible, by sequence comparisons, to identify positions at which the protein may possibly be stabilized by directed mutagenesis.

Generation of a large number of randomly selected mutations with subsequent selection for the desired property is referred to as directed evolution. The advantage of directed evolution is that knowledge about the structure of a protein or about the interactions important for folding and stability is not a precondition. In line with Darwin's "survival of the fittest" there is cumulation of the mutants which come closest to the property which is being selected for. Two important preconditions must be met for application of directed evolution. In the first place, the property which is being selected for must in fact be selectable and, in the second place, it is necessary for the selected protein variants to be coupled with the nucleotide sequences coding for them. If it is possible to select for an activity necessary for growth of a microorganism (e.g antibiotic resistance), both conditions are met. Only those microorganisms which have developed this activity multiply. In order to achieve stabilization of proteins from mesophilic organisms, it is possible to incorporate them into a thermophilic organism and then to allow the latter to grow at appropriately elevated temperature. However, this method is applicable for only a few proteins because a precondition thereof is that the protein has an activity which is distinctly advantageous or even necessary for growth of the thermophilic organism. If the proteins to be stabilized do not have such an activity (which applies to most biocatalysts and, in particular, to proteins in medical therapy and diagnosis), it is necessary to carry out the selection indirectly or in vitro. Since in this case the proteins are separated from the organisms producing them there is initially the important problem of linkage to the nucleotide sequences encoding them. Various systems have been developed in the form of phage display (Smith, G. P., 1991, Patent WO 92/01047), cell surface display (Georgiou, G. et al., 1997), ribosome display (Mattheakis, L. C. et al., 1996, Hanes, J. and Plückthun, A., 1997), repressor display (Cull, M. G. et al., 1992) and selectively infectious phage display (SIP) (Krebber, C. et al., 1995, patent application EP 94102334) to make this coupling possible. However, application of these systems is essentially confined to the selection of binding properties, in particular that of single chain antibody fragments.

It is an object of the present invention to make the potential of directed evolution available for stabilizing proteins. Thus, the aim is to develop a method which makes it possible to select out of a large number of randomly generated mutants of any protein those having increased stability.

We have found that this object is achieved by the method presented here. It makes it possible for directed evolution to be used as method for stabilizing proteins. The selection criteria used for the thermodynamic stability is the resistance of a protein to proteolytic degradation, i.e. the stability to proteases. As described above, the various types of stability are closely interconnected. In particular, the correlation between protease resistance and thermodynamic stability has also been explicitly shown (Parsell, D. A. and Sauer, R. T., 1989). Coupling of the protein to its coding sequence is ensured by the fact that it is presented on the surface of an infectious replicable gene package (e.g. of a filamentous bacteriophage) (Krebber, C. et al., 1995, patent application EP 94102334).

DETAILED DESCRIPTION OF THE INVENTION

The invention described herein makes it possible to select those phages (from a repertoire of specifically modified phages which present on their surface a particular protein) which present the most stable variants of this protein.

More generally stated, the invention described herein relates to a novel method for selecting a gene. In this connection, its ability for replication is coupled to the stability of the protein (PT) which is encoded by said gene. Gene and protein form part of an infectious replicable gene package (IRG) which can be replicated after it has infected a suitable host organism. An IRG can be, for example, a filamentous bacteriophage which infects a bacterial cell. The term stability in "stability of the protein" relates primarily to the thermodynamic stability of the protein. Further included therein are other forms of stability, such as resistance to thermal or solvent-dependent inactivation of any enzymic activity of the protein, resistance to aggregation, resistance to proteolytic cleavage by proteases and stability of a complex with a ligand.

Figure 1B:
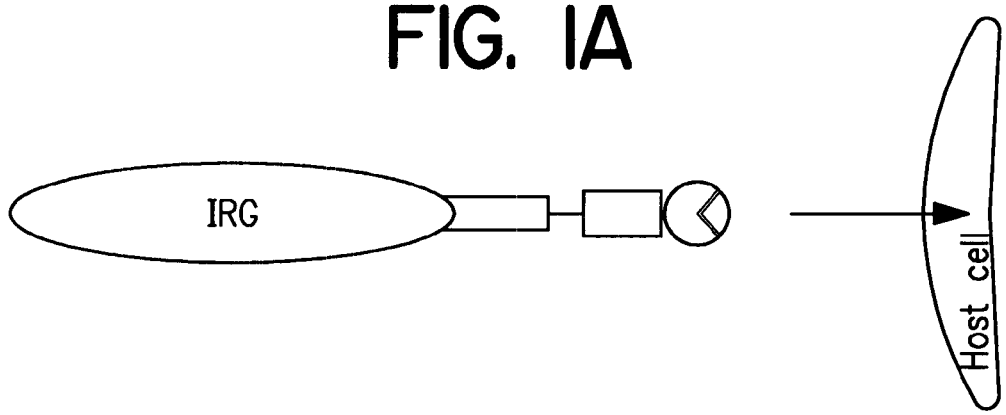
Figure 1C:
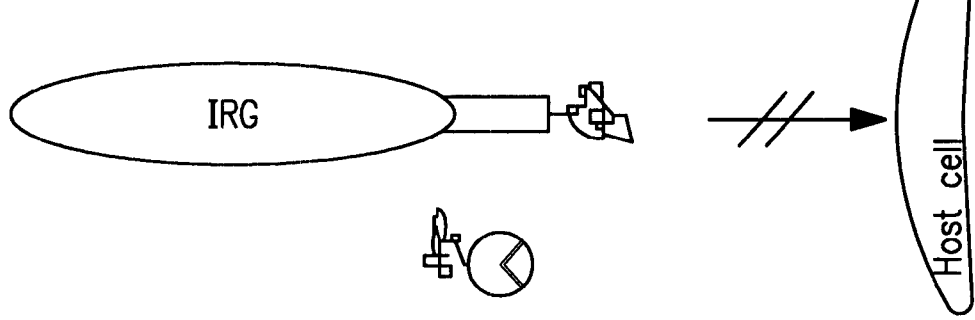

The invention comprises the following:

1.) An IRG is modified in such a way that a protein (PT) is incorporated between domains of a protein necessary for its infectivity, specifically in such a way that when said domains are separated from one another, e.g. by proteolytic cleavage of the incorporated protein (PT), the infectivity of the IRG is lost (FIG. 1). If the IRG is a filamentous bacteriophage, this can be achieved by incorporating a PT between the C-terminal domain and the N-terminal domains in all copies of the gene III protein necessary for the infection.

2.) Standard mutagenesis methods are used to generate variants of the genetic material of the IRGs which differ specifically by alteration in the sequence (both nucleotide sequence and amino acid sequence resulting therefrom) of PT. Generation of a large repertoire of variants (gene library) is typical in this connection.

3.) The genetic material is expressed in recombinant host organisms to produce IRGs which harbor PT as fusion proteins within the proteins necessary for the infection.

4.) The IRGs are incubated under particular solvent conditions with which some of the PTs are partly in denatured form. Said incubation takes place in the presence of protease in the solvent or, alternatively, said incubation without protease is immediately followed by a further incubation with protease. In the former case, the protease used must be active under the particular conditions. If the incubation is divided into two, the protease does not depend on the conditions in the first incubation. Said solvent conditions relate, for example, to pH, temperature, salt concentration, proportion of organic solvent or concentration of possible ligands of PT. In the PT repertoire there are variants which, under the particular solvent conditions, are more in denatured form than are other variants, which means that they represent better substrates for proteases. Very fine adjustment of the system is possible by slight variation in the solvent conditions or else the concentration or nature of the protease, which means that even small differences in the stability of various PTs lead to distinct differences in the rate of PT cleavage. For example, the incubation can be carried out at 37° C., 100 mM potassium phosphate, pH 8.0, 0.4 mM $CaCl_2$, 2.5 µM chymotrypsin for 30 min.

Figure 2:
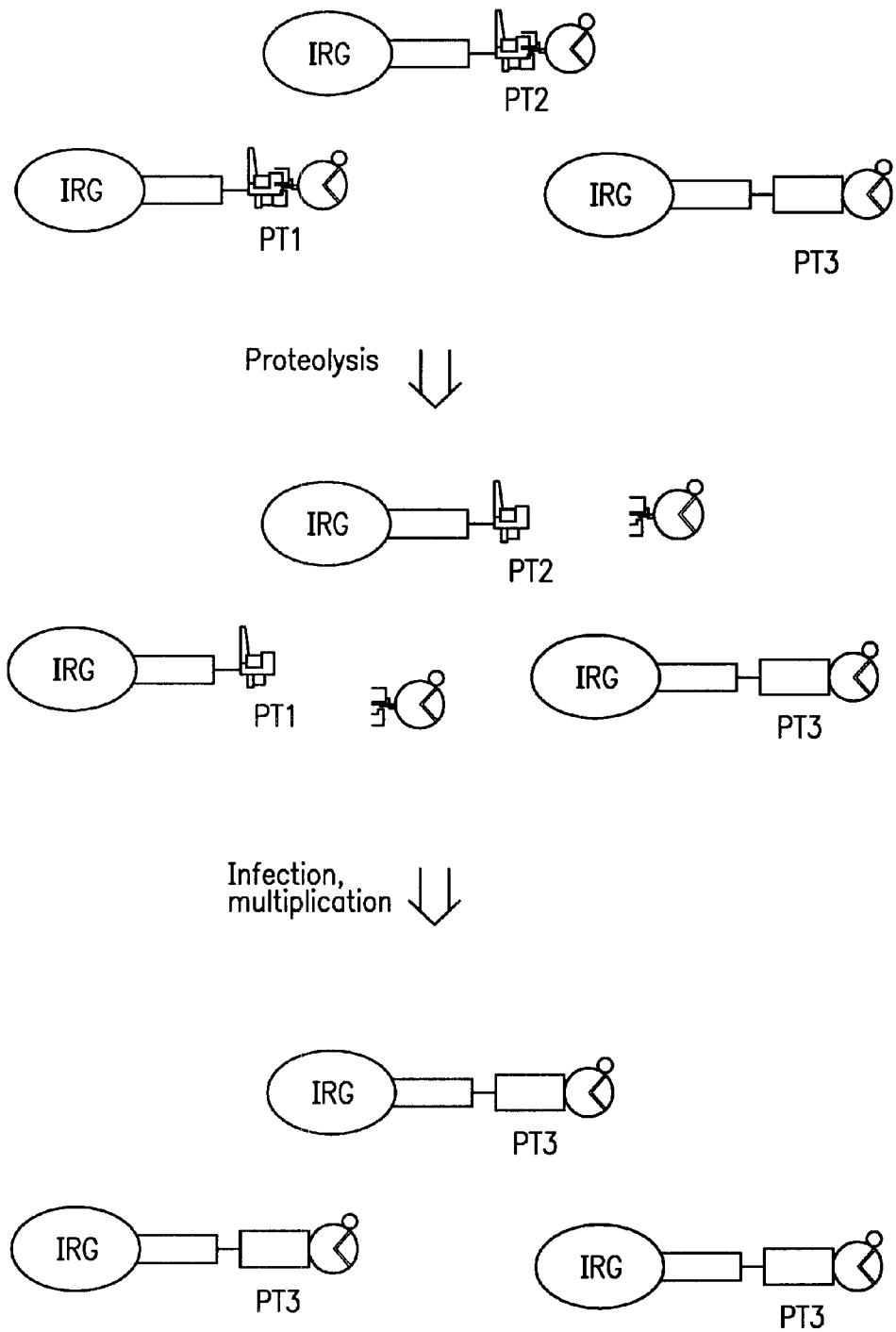

5.) Host organisms are infected with IRGs treated as under 4, and are multiplied. Only IRGs whose PTs have not been cleaved by proteases retain their infectivity and can be replicated. The host organisms produce novel IRGs which are able to go through the cycle anew so that there is enrichment of the IRGs whose PTs show the greatest stabilization (FIG. 2).

6.) The genes which encode PTs can alternatively be isolated by standard methods such as, for example, by PCR of the genome with appropriate primers. These genes can, on the one hand, be incorporated, with or without modification (e.g. mutagenesis, gene shuffling (Stemmer, W. P. C., 1994)), into the genetic material of the IRGs again, and the latter can be subjected to a new selection. On the other hand, they can also be used for PT sequence analysis.

The invention further relates also to their use for assessing the stability of a protein by determining the proteolysis-dependent rate of loss of infectivity of an IRG which has incorporated this protein on its surface as described above.

It is preferred in the invention described herein for said IRGs to be filamentous bacteriophages and for the protein necessary for the infection to be the gene III protein, in which case the proteins (PT) incorporated in the gene III protein are inserted between the C-terminal domain and the two N-terminal domains of the gene III protein. Preferred filamentous bacteriophages are specifically those of class I (fd, M13, fl, Ifl, Ike, ZJ/2 or Ff) or of class II (Xf, Pf1 or Pf3). In addition, preferred IRGs are those having in their genome no sequence sections which favor a recombination by which the incorporated genes coding for PT are eliminated. Further preferred IRGs are those which contain in their genome genes which, when expressed in the host organism, confer a growth advantage on the latter. For example, genes for antibiotic resistances can be present in the genome of the IRGs.

Further preferred PTs are globular proteins. If the stability of the PTs to be investigated is too high, they can be destabilized by targeted mutations (resulting in PT'). Based on PT', selected stabilizing mutations can be incorporated into PT. The stabilizing contributions are in most cases additive (Skinner, M. M. and Terwilliger, T. C. (1996), Wells, J. A. (1990)). It is preferred for the destabilizing mutations to result in deletion of disulfide bridges.

Preference is further given to proteases which recognize side groups of amino acids and have specific cleavage sites. Preferred in this connection are proteases which specifically cut at aromatic and/or aliphatic amino acid residues.

The generation of variants of the genetic material of the IRGs, specifically of the genes of PTs, preferably takes place by using standard methods, either of random mutagenesis or of site-specific mutagenesis.

The invention further relates to the use for a kit for selecting or for screening for genes which encode the most stable variants of proteins, which kit comprises a specifically constructed vector. This vector can be used to produce IRG and should have one or more suitable cloning sites into which DNA can be inserted. "Suitable cloning site" refers in this connection to a region of the vector in which there is at least one restriction cleavage site which can be used to insert DNA. This region should moreover be located in the coding sequence of a protein of the IRG which is necessary for the infection of a host organism by the IRG. For example, the vector pFD4Anl (see Example) can be used for this purpose. The vector should additionally have the property of being packaged as an IRG, in which case the protein (PT) or the collection of proteins (PT) which are encoded by the DNA inserted into the suitable cloning site are incorporated as fusion protein in a protein necessary for the infection of a host organism.

Further constituents of the invention described herein are defined in the claims.

EXAMPLE

Selection of Stabilized Variants of Ribonuclease T1 (RNaseT1)

1. Construction of the Phage Vector with the Gene for a Mutant of RNaseT1 (C2.6.10.103A) [RNaseT1(4A)] as Insert in Gene III (pFD4A) (see FIG. 1) and Incorporation of a New Linker (pFD4Anl)

The gene for RNaseT1(4A) was amplified by a PCR using the primers fd4ar SEQ ID NO:1 and fd4al SEQ ID NO:2.
SEQ ID NO:1 5' CGACTAGTGGCCCCCGAGGC-CGTCGCTTCAACGAAGTTG3'
SEQ ID NO:2 5' GCTCAGAGGGCCCAGCCGGCCGC-CGCGGACTACACTGC3'

The PCR product and phage vector pCKCBS (C. Krebber et al., 1997) were restricted with SfiI. The phage vector was additionally dephosphorylated with alkaline phosphatase. Cut PCR product and vector were ligated with T4 ligase and transformed into XL1-Blue E. coli cells (F') by electroporation. Part of the transformation mixture was plated out on dYTG agar (per liter of water: 16 g of peptone, 10 g of yeast extract, 5 g of NaCl, 15 g of agar, 1% glycerol, 1% glucose, 50 mM $MgCl_2$) with 25 µg/ml chloramphenicol. The phage vector pCKCBS contains the gene for chloramphenicol acetyl transferase so that bacteria which have been transformed are able to grow on chloramphenicol.

Transformants of pFD4A were identified by colony PCR, and the sequence was verified by sequencing of ss-DNA using the primer SEQ ID NO:3.

The primers SEQ ID. NO:4 and SEQ ID NO:5 and the Quickchange mutagenesis kit (Stratagene) were used to incorporate a new HincII cleavage site C-terminal of the RNaseT1 insert. After limited restriction with EcoRI and HincII and dephosphorylation with alkaline phosphatase, a new linker (fdlinkup+fdlinkdown) was ligated in, and XL1-Blue E. coli cells (F') were transformed therewith. Colony PCR was used to identify a correct transformant, and the sequence was verified by sequencing of ss-DNA using the primer SEQ ID NO:3.
SEQ ID NO:3 5' GCA TTT TCG GTC ATA GC3'
SEQ ID NO:4 5' CCTGTCAAcGCTGGCGG3'
SEQ ID NO:5 5' CCGCCAGCgTTGACAGG3'
SEQ ID NO:6 5' AATTCCCAGGTACCCCGGTT3'
SEQ ID NO:7 5' AACCGGGGTACCTGGG3'

2. Random Mutagenesis

Degenerate oligonucleotides SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and the gene SOEing method (Horton, R. M. and Pease, L. R., 1991) were used to randomize the RNaseT1(4A) gene at three positions in relation to the amino acids: position 17(S), 29(D) and 42(Y) of the RNaseT1 gene. (The amino acids indicated in parentheses are those at the corresponding position in the wild-type RNaseT1.) The incorporation of cysteine and of stop codons was moreover avoided. The primer used at the N terminus of the gene for RNaseT1(4A) was SEQ ID NO:26 and for the C terminus was SEQ ID NO:27.
SEQ ID NO:8 5' CTT CAG ACG TT(ACG) (ACGT)(GT)A CTG CTC AAG3'
SEQ ID NO:9 5' CTT GAG CAG T(AC)(ACGT) (CGT)AA CGT CTG AAG3'
SEQ ID NO:10 5' CTT CAG ACG TTT (AT)CA CTG CTC AAG3'
SEQ ID NO:11 5' CTT GAG CAG TG(AT) AAA CGT CTG AAG3'
SEQ ID NO:12 5' CTT CAG ACG TTT GGA CTG CTC AAG3'
SEQ ID NO:13 5' CTT GAG CAG TCC AAA CGT CTG AAG3'
SEQ ID NO:14 5' CTT CAC GAA (ACG)(ACGT)(GT) GGT GAA ACT G3'
SEQ ID NO:15 5' CAG TTT CAC C(AC)(ACQT) (CGT)TT CGT GAA G3'
SEQ ID NO:16 5' CTT CAC GAA T(AT)C GGT GAA ACT G3'
SEQ ID NO:17 5' CAG TTT CAC CG(AT) ATT CGT GAA G3'
SEQ ID NO:18 5' CTT CAC GAA TGG GCT GAA ACT G3'
SEQ ID NO:19 5' CAG TTT CAC CCC ATT CGT GAA G3'
SEQ ID NO:20 5' CCA CAC AAA (ACG)(ACGT)(GT) AAC AAC TAC G3'
SEQ ID NO:21 5' CGT AGT TGT T(AC)(ACGT) (CGT)TT TGT GTG G3'
SEQ ID NO:22 5' CCA CAC AAA T(AT)C AAC AAC TAC G3'
SEQ ID NO:23 5' CGT AGT TGT TG(AT) ATT TGT GTG G3'
SEQ ID NO:24 5' CCA CAC AAA TGG AAC AAC TAC G3'
SEQ ID NO:25 5' CGT AGT TGT TCC ATT TGT GTG G3'
SEQ ID NO:26 5' GCT TCA ACG AAG TTG TTA CC3'
SEQ ID NO:27 5' CAC TGC COG TTC TAA CG3'

Primers nXX-1a (XX represents positions 17, 29 and 42) code for all amino acids apart from C, Y, F, W and stop codons. Primers nXX-2a code for Y and F and primers nXX-3a code for W. Primers nXX-1/2/3b are the corresponding opposite strand primers. Primer mixtures were prepared (nXXa/b:nXX-1a/b:nXX-2a/b:nXX-3a/b=24:2:1) so that all codons are represented equally. Partial pieces of the gene were amplified by PCR using the primers rrandl+ n17b, n17a +n29b, n29a+n42b and n42a+rrandr. After purification of the PCR products from an agarose gel, about 1 pmol of each of these fragments together was used to carry out a PCR without additional primers so that the complete gene was able to assemble. The randomized gene for RNaseT1(4A) was amplified with 2.5 µl of this mixture (about 2 fmol) and the primers rrandl and rrandr.

3. Incorporation of the Randomized Genes into the Vector

Phages with RNaseT1(4A) insert were grown and the (+) strand coding for the phage vector was prepared therefrom. The PCR fragments obtained from 2.) were annealed as primers onto the (+) strand of the phage DNA, the (−) strand was synthesized with Pfu polymerase, the ends of the (−) strand were ligated with T4 ligase, and the ss-DNA still present in the mixture was degraded with mung bean nuclease. The ds-DNA of the phase (RF form) obtained in this way was transformed by electroporation into XL1-Blue cells, and the bacteria were plated out. The transformants (about $10^6$) were used to inoculate dYTG medium (25 µg/ml chloramphenicol), and phages were prepared from the medium.

4. Selection Step

These phages were used to infect XL1-Blue cells, and phages were prepared again after renewed amplification. About $10^{10}$ phages were incubated in 100 mM potassium phosphate, pH 7.5, 0.4 M NaCl, and 0.4 mM $CaCl_2$ with 0.25 µM chymotrypsin in 50 µl at 15° C. for 30 min. This 50 µl was then used to infect 5 ml of XL1-Blue cells (OD about 1.0). The latter were amplified in dYTG medium with 25 µg/ml chloramphenicol over night. The RF form, of the phage DNA was isolated from 1.5 ml of bacterial suspension the next morning. Starting from this DNA and the primers rrandr and rrandl, the genes of the various mutants of RNaseT1(4A) which had survived the first round of selection were amplified by PCR. The fragments obtained in this way were incorporated again into the phage vector (see 3.).

5. Analysis

After a total of 4 cycles of incorporation, amplification and selection, infected bacteria were isolated, phages were amplified from the latter and isolated, and ss-DNA was prepared and sequenced. 5 of the 10 mutants obtained in this way were identical in their amino acid sequence but not in nucleotide sequence (A17, L29, F42), and 4 of the remaining 5 likewise had an F at position 42, three had an A at position 17, two had an A at position 29, one had an L at position 17, and one each had a D and an R at position 29. A wild-type gene was found.

Figure 3:
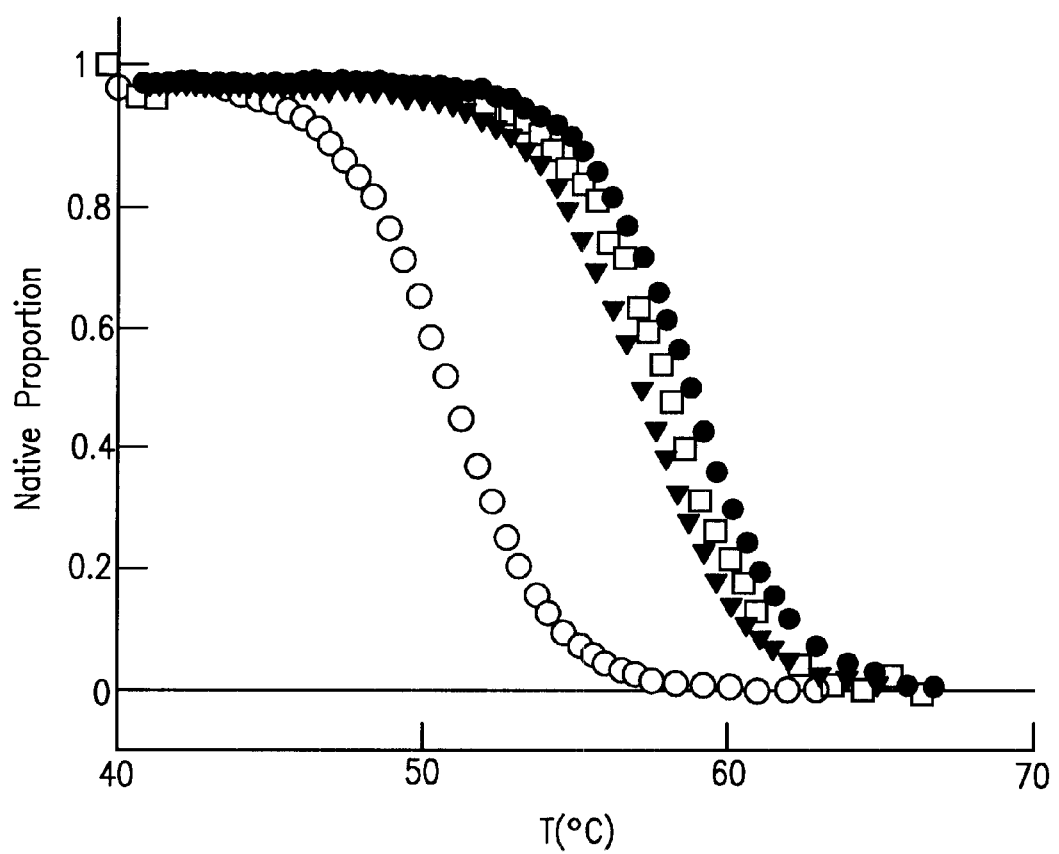

In 3 variants (L17, A29, F42; A17, A29, F42 and A17, L29, F42) positions 2, 6, 10 and 103 were converted back into cysteine, and protein was purified and investigated for thermodynamic stability. The mutants obtained in this way showed increases in the mid point of the thermal unfolding transition by 6.2° C., 7.0° C. and 7.8° C. (resp.) (FIG. 3). This corresponds to an increase in stability at 50° C. relative to wild-type RNaseT1 by about 9 kJ/mol, 10 kJ/mol and 12 kJ/mol, respectively.

After further cycles, only the variant A17, L29, F42 was detectable and showed the greatest stabilization of the variants investigated. It can be assumed that this variant is the most stable from the limited repertoire of about 6000.

LIST OF REFERENCES

Bowie, J. U. and Eisenberg, D. (1993) *Curr. Opin. Stuct. Biol.* 3, 437–444

Brems, D. N., Brown, P. L., Bryant, C., Chance, R. E., Green, L. K., Long, H. B., Miller, A. A., Millican, R., Shields, J. E. and Frank, B. H. (1992) *Protein Eng.* 5, 519–525

Cabral, J. M. S. and Kennedy, J. F., (1993) in *Thermostability of Enzymes* (ed. Gupta, M. N.) Springer Verlag, Berlin.

Cull, M. G. Miller, J. F. and Schatz, P. J. (1992) *Proc. Natl. Acad. Sci. USA* 89, 1865–69

Fischer, D. and Eisenberg, D. (1996) *Protein Sci.* 5, 947–55

Gates, C. M., Stemmer, W. P., Kaptein, R. and Schatz, P. J. (1996), *J. Mol. Biol.* 255(3) 373–86

Georgiou, G., Stathopoulos, C., Daugherty, P. S., Nayak, A. R. Iverson, B. L. and Curtiss III, R. (1997) *Nature Biotech.* 5, 29–34

Gray, C. J. (1993) in *Thermostability of Enzymes* (ed. Gupta, M. N.) Springer Verlag, Berlin Gupta, S. and Gupta, M. N. (1993) in *Thermostability of Enzymes* (ed. Gupta, M. N.) Springer Verlag, Berlin Hanes, J. and Plückthun, A. (1997) *Proc. Natl. Acad. Sci. USA* 94, 4937–42

Horton, R. M. and Pease, L. R. (1991) in *Directed Mutagenesis—A Practical Approach* (ed. McPherson, M. J.) IRL Press, Oxford Imoto, T. (1997) *CMLS, Cell. mol. life sci.* 53, 215–223

Krebber, C., Spada, S., Desplancq, D. and Plückthun, A. (1995) *FEBS Letters* 377, 227–31

Krebber, C., Spada, S., Desplancq, D., Krebber, A.; Ge, L. and Plückthun, A. (1997) *J. Mol. Biol.* 268(3), 607–18

Mattheakis, L. C., Dias, J. M. and Dower, W. J. (1996) *Meth. Enz.* 267, 195–207

Matthews, D. J. and Wells, J. (1993), *Science* 260, 1113–7

Martinek, K. and Mozhanev, V. V. (1993) in *Thermostability of Enzymes* (ed. Gupta, M. N.) Springer Verlag, Berlin Pace, C. N., Shirley, B. A., McNutt, M and Gajwala, K. (1996) *FASEB J.* 10, 75–83

Parsell, D. A. and Sauer, R. T. (1989) *J. Biol. Chem.* 264, 7590–7595

Shoichet, B. K., Baase, W. A., Kuroki, R. and Matthews, B. W. (1995) *Proc. Natl. Acad. Sci. USA* 92, 452–6.

Skinner, M. M. and Terwilliger, T. C. (1996) *Proc. Natl Acad. Sci. USA* 93, 10753–7

Smith, G. P. (1991) *Curr. Opin. Biotechnol.* 2, 668

Stemmer, W. P. C. (1994) *Nature* 370, 389–91

Tyagi, R. and Gupta, M. N. (1993) in *Thermostability of Enzymes* (ed. Gupta, M. N.) Springer Verlag, Berlin Wells, J. A. (1990) *Biochemistry* 29, 8517–21

Patent WO 92/01047

Patent application EP 94102334

FIG. 1 (Panels A–C) Diagrammatic representation of the incorporation of a protein (PT) into a protein necessary for the infection of an IRG and, following from this, the option of loss of infectivity of the IRG. IRGs without incorporated protein (PT) or with intact incorporated protein (PT) (A and B) are able to infect host cells. IRGs whose incorporated protein (PT) has been proteolytically cleaved (C) are no longer able to infect bacterial cells.

FIG. 2 Diagrammatic representation of the enrichment of a more stable variant of PT after one round of selection. After the proteolysis (A), only IRGs with the protein variant PT3 are still able to infect bacterial cells (B) and are multiplied and enriched.

FIG. 3 Thermal unfolding transition of three mutants obtained using the method to be patented on RNaseT1. The proportion of native protein, measured by the change in absorption at 286 nm relative to 274 nm, is plotted as a function of time. The mid points of the transitions are at 50.9° C. (S17, D29, Y42=wild-type) (○), 57.1° C. (L17, A29, F42) (▼), 57.9° C. (A17, A29, F42) (□) and 58.7° C. (A17, L29, F42) (●). The identification of the stabilized variants is derived from the identification of the amino acids found at positions 17, 29 and 42 (one-letter code).

Figure 4:
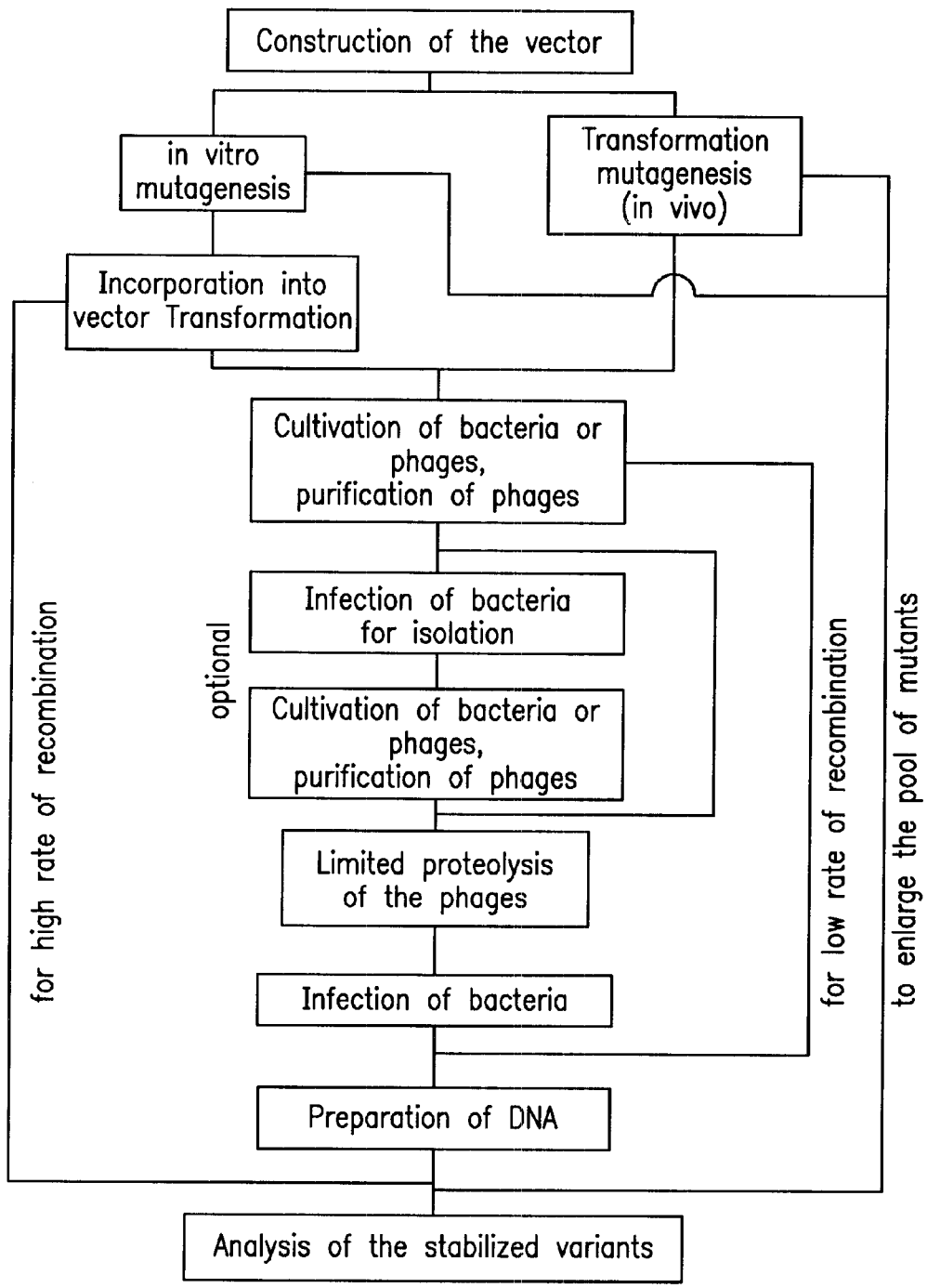

FIG. 4 Flow diagram of a typical application of the method.

We claim:

1. A method for selecting genes which code for stabilized proteins, which comprises the following steps:
   a) modification of an infectious replicable gene package (IRG) so that its infection of a host cell can be suppressed, as described under (b) and (d);
   b) insertion of DNA sequences which code for a repertoire of mutants of a protein (PT) into the genome of the IRG so that said mutants of the protein (PT) are incorporated as fusion proteins in a protein necessary for infection of a host organism;
   c) expression of the IRGs with a repertoire of mutants of the protein (PT) in a recombinant host organism;
   d) subjection of the IRGs to partial proteolysis during or after incubation under solvent conditions which influence the conformational stability of the protein (PT) so that the IRGs which are not stable under said solvent conditions are cleaved during the partial proteolysis and therefore loose their infectivity, and so that the IRGs which are stable under said solvent conditions and therefore not cleaved during the partial proteolysis retain their infectivity, and wherein the partial proteolysis and incubation are done in the presence of a ligand, inhibitor or substrate analog for the protein (PT);
   e) infection of host organisms after treatment according to (d) and amplification of the host organisms;
   f) isolation of IRGs which contain genes which code for stable proteins (PT) from said host organisms;
   g) use of the recovered IRGs repeatedly in the complete process from (b) to (f);
   h) isolation of the genes from the recovered IRGs.

2. The method as claimed in claim 1 (a) to (d) and the further steps:
   e') analysis of the remaining infectivity of IRGs treated as under 2 (d);
   f') isolation of the genes from selected IRGs depending on the result of (e').

3. The method as claimed in claim 1, wherein the IRG of step (a) has itself has been subjected to a selection whereby its stability has been increased and its infectivity is influenced less by extreme conditions wherein the extreme conditions are selected from the group consisting of pH<2, pH>10 and temperature above 50° C.

4. The method as claimed in claim 1, wherein the IRGs used have in their genome, on both sides of the inserted DNA sequences, no sequence repeats favoring recombination.

5. The method as claimed in claim 1 wherein the IRG is a filamentous bacteriophage selected from the group consisting of fd, M13, f1, If1, ZJ/2, Ff, Xf, Pf1 and Pf3.

6. The method as claimed in claim 1, wherein the host organisms for infection by the IRGs have a recombination deficiency, and this deficiency is in RecA, RecB, RecC or combinations thereof RecD when *E. coli* cells are used as host organisms.

7. The method as claimed in claim 1 wherein the protein which is necessary for the infectivity of a host organism is the gene III protein of a filamentous phage.

8. The method as claimed in claim 1 wherein the protein (PT) is selected from the group consisting of an enzyme, subunit of a multidomain enzyme, ligand-binding protein and a receptor-binding protein.

9. The method as claimed in claim 1, wherein a protease which recognizes principally aromatic and aliphatic amino acid residues is used in 2 (d).

10. The method as claimed in claim 1, wherein a metalloprotease, serine protease, threonine protease, cysteine protease or acid protease is the protease in 2(d).

11. A method as claimed in claim 10, wherein the protease is chymotrypsin, trypsin or pepsin.

12. The method as claimed in claim 1, wherein mutants of the protein (PT) are obtained which have a characteristic selected from the group consisting of increased thermodynamic stability, increased resistance to proteases, increased resistance to irreversible thermal activation, increased resistance to aggregation, increased interaction with ligands, increased interaction with substrates, and combinations thereof, wherein the characteristic is increased relative to the respective wild-type form of the protein (PT).

13. The method as claimed in claim 1, wherein a directed or random mutagenesis of the DNA sequences coding for the protein (PT) is carried out.

14. The method as claimed in claim 13, wherein the mutagenesis is achieved by DNA oligonucleotide cassette mutagenesis.

15. The method as claimed in claim 13, wherein the mutagenesis is achieved by using a mutator bacterial strain.

16. A method as claimed in claim 15, wherein said bacterial mutator strain is an *E. coli* strain with a deficiency in mutD, mutH, mutL, mutS or mutT.

17. The method as claimed in claim 13, wherein the mutagenesis is achieved by using a mutagen during multiplication of a host organism.

18. The method as claimed in claim 13, wherein the random mutagenesis takes place by error-prone PCR of said DNA sequences.

* * * * *

UNITED STATES PATENT AND TRADEMARK OFFICE
CERTIFICATE OF CORRECTION

PATENT NO.    : 6,468,746 B1                                     Page 1 of 1
DATED         : October 22, 2002
INVENTOR(S)   : Sieber et al.

It is certified that error appears in the above-identified patent and that said Letters Patent is hereby corrected as shown below:

Column 18,
Lines 62-63, "RecA, RecB, RecC or combinations therefor RecD" should be
-- *RecA, RecB, RecC, RecD*, or combinations therefor --.

Column 20,
Line 11, "bacterial mutator" should be -- mutator bacterial --.
Line 12, "mutD, mutH, mutL, mutS, or mutT"should be
-- *mutD, mutH, mutL, mutS, or mutT* --.

Signed and Sealed this

Eighteenth Day of February, 2003

JAMES E. ROGAN
*Director of the United States Patent and Trademark Office*

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
        (A) LENGTH: 39 nucleic acids
        (B) TYPE: Nucleic acid
        (C) STRANDEDNESS: single
        (D) TOPOLOGY: linear (xi) SEQUENCE DESCRIPTION: SEQ ID NO: 1:

CGACTAGTGG CCCCCGAGGC CGTCGCTTCA ACGAAGTTG                              39

(2) INFORMATION FOR SEQ ID NO: 2:

(i) SEQUENCE CHARACTERISTICS:
        (A) LENGTH: 38 nucleic acids
        (B) TYPE: Nucleic acid
        (C) STRANDEDNESS: single
        (D) TOPOLOGY: linear (xi) SEQUENCE DESCRIPTION: SEQ ID NO: 2:

GCTCAGAGGG CCCAGCCGGC CGCCGCGGAC TACACTGC                               38

(2) INFORMATION FOR SEQ ID NO: 3:

(i) SEQUENCE CHARACTERISTICS:
        (A) LENGTH: 17 nucleic acids
        (B) TYPE: Nucleic acid
        (C) STRANDEDNESS: single
        (D) TOPOLOGY: linear (xi) SEQUENCE DESCRIPTION: SEQ ID NO: 3:

GCATTTTCGG TCATAGC                                                      17

(2) INFORMATION FOR SEQ ID NO: 4:

(i) SEQUENCE CHARACTERISTICS:
        (A) LENGTH: 17 nucleic acids
        (B) TYPE: Nucleic acid
        (C) STRANDEDNESS: single
        (D) TOPOLOGY: linear (xi) SEQUENCE DESCRIPTION: SEQ ID NO: 4:

CCTGTCAACG CTGGCGG                                                      17

(2) INFORMATION FOR SEQ ID NO: 5:

(i) SEQUENCE CHARACTERISTICS:
        (A) LENGTH: 17 nucleic acids
        (B) TYPE: Nucleic acid
        (C) STRANDEDNESS: single
        (D) TOPOLOGY: linear (xi) SEQUENCE DESCRIPTION: SEQ ID NO: 5:

CCGCCAGCGT TGACAGG                                                      17

(2) INFORMATION FOR SEQ ID NO: 6:

(i) SEQUENCE CHARACTERISTICS:
        (A) LENGTH: 20 nucleic acids
        (B) TYPE: Nucleic acid
        (C) STRANDEDNESS: single (D) TOPOLOGY: linear (xi) SEQUENCE DESCRIPTION: SEQ ID NO: 6:

AATTCCCAGG TACCCCGGTT                                                    20

(2) INFORMATION FOR SEQ ID NO: 7:

(i) SEQUENCE CHARACTERISTICS:
        (A) LENGTH: 16 nucleic acids
        (B) TYPE: Nucleic acid
        (C) STRANDEDNESS: single
        (D) TOPOLOGY: linear (xi) SEQUENCE DESCRIPTION: SEQ ID NO: 7:

AACCGGGGTA CCTGGG                                                        16

(2) INFORMATION FOR SEQ ID NO: 8:

(i) SEQUENCE CHARACTERISTICS:
        (A) LENGTH: 30 nucleic acids
        (B) TYPE: Nucleic acid
        (C) STRANDEDNESS: single
        (D) TOPOLOGY: linear (xi) SEQUENCE DESCRIPTION: SEQ ID NO: 8:

CTTCAGACGT TACGACGTGT ACTGCTCAAG                                          30

(2) INFORMATION FOR SEQ ID NO: 9:

(i) SEQUENCE CHARACTERISTICS:
        (A) LENGTH: 30 nucleic acids
        (B) TYPE: Nucleic acid
        (C) STRANDEDNESS: single
        (D) TOPOLOGY: linear (xi) SEQUENCE DESCRIPTION: SEQ ID NO: 9:

CTTGAGCAGT ACACGTCGTA ACGTCTGAAG                                          30

(2) INFORMATION FOR SEQ ID NO: 10:

(i) SEQUENCE CHARACTERISTICS:
        (A) LENGTH: 25 nucleic acids
        (B) TYPE: Nucleic acid
        (C) STRANDEDNESS: single
        (D) TOPOLOGY: linear (xi) SEQUENCE DESCRIPTION: SEQ ID NO: 10:

CTTCAGACGT TTATCACTGC TCAAG                                               25

(2) INFORMATION FOR SEQ ID NO: 11:

(i) SEQUENCE CHARACTERISTICS:
        (A) LENGTH: 25 nucleic acids
        (B) TYPE: Nucleic acid
        (C) STRANDEDNESS: single
        (D) TOPOLOGY: linear (xi) SEQUENCE DESCRIPTION: SEQ ID NO: 11:

CTTGAGCAGT GATAAACGTC TGAAG                                               25

(2) INFORMATION FOR SEQ ID NO: 12:

(i) SEQUENCE CHARACTERISTICS:
        (A) LENGTH: 24 nucleic acids
        (B) TYPE: Nucleic acid
        (C) STRANDEDNESS: single
        (D) TOPOLOGY: linear (xi) SEQUENCE DESCRIPTION: SEQ ID NO: 12:

CTTCAGACGT TTGGACTGCT CAAG                                    24

(2) INFORMATION FOR SEQ ID NO: 13:

(i) SEQUENCE CHARACTERISTICS:
        (A) LENGTH: 24 nucleic acids
        (B) TYPE: Nucleic acid
        (C) STRANDEDNESS: single
        (D) TOPOLOGY: linear (xi) SEQUENCE DESCRIPTION: SEQ ID NO: 13:

CTTGAGCAGT CCAAACGTCT GAAG                                    24

(2) INFORMATION FOR SEQ ID NO: 14:

(i) SEQUENCE CHARACTERISTICS:
        (A) LENGTH: 28 nucleic acids
        (B) TYPE: Nucleic acid
        (C) STRANDEDNESS: single
        (D) TOPOLOGY: linear (xi) SEQUENCE DESCRIPTION: SEQ ID NO: 14:

CTTCACGAAA CGACGTGTGG TGAAACTG                                28

(2) INFORMATION FOR SEQ ID NO: 15:

(i) SEQUENCE CHARACTERISTICS:
        (A) LENGTH: 28 nucleic acids
        (B) TYPE: Nucleic acid
        (C) STRANDEDNESS: single
        (D) TOPOLOGY: linear (xi) SEQUENCE DESCRIPTION: SEQ ID NO: 15:

CAGTTTCACC ACACGTCGTT TCGTGAAG                                28

(2) INFORMATION FOR SEQ ID NO: 16:

(i) SEQUENCE CHARACTERISTICS:
        (A) LENGTH: 23 nucleic acids
        (B) TYPE: Nucleic acid
        (C) STRANDEDNESS: single
        (D) TOPOLOGY: linear (xi) SEQUENCE DESCRIPTION: SEQ ID NO: 16:

CTTCACGAAT ATCGGTGAAA CTG                                     23

(2) INFORMATION FOR SEQ ID NO: 17:

(i) SEQUENCE CHARACTERISTICS:
        (A) LENGTH: 23 nucleic acids
        (B) TYPE: Nucleic acid
        (C) STRANDEDNESS: single
        (D) TOPOLOGY: linear (xi) SEQUENCE DESCRIPTION: SEQ ID NO: 17:

CAGTTTCACC GATATTCGTG AAG                                     23

(2) INFORMATION FOR SEQ ID NO: 18:

(i) SEQUENCE CHARACTERISTICS:
        (A) LENGTH: 22 nucleic acids
        (B) TYPE: Nucleic acid
        (C) STRANDEDNESS: single
        (D) TOPOLOGY: linear (xi) SEQUENCE DESCRIPTION: SEQ ID NO: 18:

CTTCACGAAT GGGGTGAAAC TG                                    22

(2) INFORMATION FOR SEQ ID NO: 19:

(i) SEQUENCE CHARACTERISTICS:
        (A) LENGTH: 22 nucleic acids
        (B) TYPE: Nucleic acid
        (C) STRANDEDNESS: single
        (D) TOPOLOGY: linear (xi) SEQUENCE DESCRIPTION: SEQ ID NO: 19:

CAGTTTCACC CCATTCGTGA AG                                    22

(2) INFORMATION FOR SEQ ID NO: 20:

(i) SEQUENCE CHARACTERISTICS:
        (A) LENGTH: 28 nucleic acids
        (B) TYPE: Nucleic acid
        (C) STRANDEDNESS: single
        (D) TOPOLOGY: linear (xi) SEQUENCE DESCRIPTION: SEQ ID NO: 20:

CCACACAAAA CGACGTGTAA CAACTACG                              28

(2) INFORMATION FOR SEQ ID NO: 21:

(i) SEQUENCE CHARACTERISTICS:
        (A) LENGTH: 28 nucleic acids
        (B) TYPE: Nucleic acid
        (C) STRANDEDNESS: single
        (D) TOPOLOGY: linear (xi) SEQUENCE DESCRIPTION: SEQ ID NO: 21:

CGTAGTTGTT ACACGTCGTT TTGTGTGG                              28

(2) INFORMATION FOR SEQ ID NO: 22:

(i) SEQUENCE CHARACTERISTICS:
        (A) LENGTH: 23 nucleic acids
        (B) TYPE: Nucleic acid
        (C) STRANDEDNESS: single
        (D) TOPOLOGY: linear (xi) SEQUENCE DESCRIPTION: SEQ ID NO: 22:

CCACACAAAT ATCAACAACT ACG                                   23

(2) INFORMATION FOR SEQ ID NO: 23:

(i) SEQUENCE CHARACTERISTICS:
        (A) LENGTH: 23 nucleic acids
        (B) TYPE: Nucleic acid
        (C) STRANDEDNESS: single
        (D) TOPOLOGY: linear (xi) SEQUENCE DESCRIPTION: SEQ ID NO: 23:

CGTAGTTGTT GATATTTGTG TGG                                   23

(2) INFORMATION FOR SEQ ID NO: 24:

(i) SEQUENCE CHARACTERISTICS:
        (A) LENGTH: 22 nucleic acids
        (B) TYPE: Nucleic acid
        (C) STRANDEDNESS: single
        (D) TOPOLOGY: linear (xi) SEQUENCE DESCRIPTION: SEQ ID NO: 24:

-continued

```
CCACACAAAT GGAACAACTA CG                                               22

(2) INFORMATION FOR SEQ ID NO: 25:

(i) SEQUENCE CHARACTERISTICS:
        (A) LENGTH: 21 nucleic acids
        (B) TYPE: Nucleic acid
        (C) STRANDEDNESS: single
        (D) TOPOLOGY: linear (xi) SEQUENCE DESCRIPTION: SEQ ID NO: 25:

CGTAGTGTT CCATTTGTGT GG                                                21

(2) INFORMATION FOR SEQ ID NO: 26:

(i) SEQUENCE CHARACTERISTICS:
        (A) LENGTH: 20 nucleic acids
        (B) TYPE: Nucleic acid
        (C) STRANDEDNESS: single
        (D) TOPOLOGY: linear (xi) SEQUENCE DESCRIPTION: SEQ ID NO: 26:

GCTTCAACGA AGTTGTTACC                                                  20

(2) INFORMATION FOR SEQ ID NO: 27:

(i) SEQUENCE CHARACTERISTICS:
        (A) LENGTH: 17 nucleic acids
        (B) TYPE: Nucleic acid
        (C) STRANDEDNESS: single
        (D) TOPOLOGY: linear (xi) SEQUENCE DESCRIPTION: SEQ ID NO: 27:

CACTGCCGGT TCTAACG                                                     17
```